US011197656B2

(12) United States Patent
Guo et al.

(10) Patent No.: US 11,197,656 B2
(45) Date of Patent: Dec. 14, 2021

(54) PULSED DOPPLER ULTRA-HIGH SPECTRAL RESOLUTION IMAGING PROCESSING METHOD AND PROCESSING SYSTEM

(71) Applicant: VINNO TECHNOLOGY (SUZHOU) CO., LTD., Suzhou (CN)

(72) Inventors: Jianjun Guo, Suzhou (CN); Huiren Chen, Suzhou (CN)

(73) Assignee: VINNO TECHNOLOGY (SUZHOU) CO., LTD, Suzhou (CN)

( * ) Notice: Subject to any disclaimer, the term of this patent is extended or adjusted under 35 U.S.C. 154(b) by 445 days.

(21) Appl. No.: 16/304,268

(22) PCT Filed: Feb. 16, 2017

(86) PCT No.: PCT/CN2017/073774
§ 371 (c)(1),
(2) Date: Nov. 23, 2018

(87) PCT Pub. No.: WO2017/202068
PCT Pub. Date: Nov. 30, 2017

(65) Prior Publication Data
US 2019/0083066 A1    Mar. 21, 2019

(30) Foreign Application Priority Data
May 26, 2016    (CN) .......................... 201610356317.8

(51) Int. Cl.
*A61B 8/00*    (2006.01)
*A61B 8/08*    (2006.01)
(Continued)

(52) U.S. Cl.
CPC ............... *A61B 8/488* (2013.01); *A61B 8/06* (2013.01); *A61B 8/5207* (2013.01);
(Continued)

(58) Field of Classification Search
CPC ... A61B 8/4427; A61B 8/4422; A61B 8/4472; A61B 8/4483; A61B 8/06; A61B 8/462; A61B 8/463; A61B 8/488; A61B 8/56
See application file for complete search history.

(56) References Cited

U.S. PATENT DOCUMENTS

| 6,390,984 B1 * | 5/2002 | Pan .......................... A61B 8/06 600/453 |
| 2012/0059264 A1 * | 3/2012 | Hope Simpson ...... A61B 8/488 600/454 |
| 2015/0324957 A1 | 11/2015 | Honjo et al. |

FOREIGN PATENT DOCUMENTS

| CN | 1561916 A | 1/2002 |
| CN | 103142253 A | 6/2013 |

(Continued)

OTHER PUBLICATIONS

International Search Report for PCT/CN2017/073774 dated May 24, 2017 and its English translation provided by WIPO.

(Continued)

*Primary Examiner* — Michael J Tsai
*Assistant Examiner* — Adam D. Kolkin
(74) *Attorney, Agent, or Firm* — Ladas & Parry, LLP (57) ABSTRACT

The present invention provides a pulsed Doppler ultra-high spectral resolution imaging processing method and processing system. The method includes: acquiring IQ signals corresponding to N sampling points respectively on each scan line; in a fast time direction, performing wall filtering processing to form an IQ signal wall filtering sequence; performing FFT on each sampling point in the IQ signal wall filtering sequence in a slow and a fast time direction, respectively, to obtain an energy distribution matrix at different frequency shifts; acquiring a velocity distribution matrix; and retrieving a velocity sequence for display, querying the velocity distribution matrix and the energy distri- (Continued)

bution matrix according to the velocity sequence, and acquiring an energy sequence corresponding to the velocity sequence for displaying a final spectrum. When a transmit signal bandwidth is wider or a scatterer velocity is faster, the velocity resolution is greatly guaranteed.

4 Claims, 4 Drawing Sheets

(51) Int. Cl.
    *A61B 8/06*     (2006.01)
    *G01S 15/89*     (2006.01)
    *G01S 7/52*     (2006.01)
    *G06T 7/00*     (2017.01)

(52) U.S. Cl.
    CPC ...... *G01S 7/52047* (2013.01); *G01S 7/52066* (2013.01); *G01S 15/8977* (2013.01); *G06T 7/0012* (2013.01); *G06T 2207/10132* (2013.01); *G06T 2207/20056* (2013.01); *G06T 2207/30004* (2013.01)

(56) References Cited

FOREIGN PATENT DOCUMENTS

| | | | |
|---|---|---|---|
| CN | 105476665 A | 4/2016 | |
| WO | WO-03050760 A1 * | 6/2003 | ............. G06T 5/002 |

OTHER PUBLICATIONS

Written Opinion of the International Search Authority for PCT/CN2017/073774 dated May 24, 2017 and its English translation provided by Google Translate.

\* cited by examiner

PULSED DOPPLER ULTRA-HIGH SPECTRAL RESOLUTION IMAGING PROCESSING METHOD AND PROCESSING SYSTEM

CROSS-REFERENCE TO RELATED APPLICATIONS

The present application is the U.S. national phase of PCT/CN2017/073774 filed on Feb. 16, 2017, which claims the priority of Chinese patent application No, 201610356317.8 filed on May 26, 2016 and entitled "Pulsed Doppler Ultra-high Spectral Resolution Imaging Processing Method and Processing System", the disclosures of which are incorporated herein by reference.

TECHNICAL FIELD

The present invention belongs to the technical field of medical ultrasound, and mainly relates to a pulsed Doppler ultra-high spectral resolution imaging processing method and processing system.

BACKGROUND

Ultrasound imaging has become one of the most widely used diagnostic methods in clinical practice because of its non Invasive, real-time, easy-to-operate, and low price advantages. Pulsed Doppler imaging can conveniently and quickly measure the specific flow rate of a blood flow, which is the criterion for certain diseases in clinical diagnosis.

In the conventional pulsed Doppler processing technology, one-dimensional Fourier transform is performed on an echo signal in a slow time direction to obtain a frequency shift distribution and the energy of the echo signal. According to the frequency shift distribution and a center frequency of a transmit signal, a corresponding velocity is calculated. The conventional pulsed Doppler processing technology is based on the Doppler effect. The magnitude of the frequency shift caused by the motion of a scatterer is proportional to the product of the frequency of the transmit signal and the motion velocity of the scatterer. Thus, in the conventional pulsed Doppler processing technology, due to the non-uniformity of the velocity spectrum, a fast scatterer has a wide frequency shifting bandwidth and poor spectral resolution, while a slow scatterer has a narrow frequency shifting bandwidth and good spectral resolution. Meanwhile, the Doppler spectral resolution is greatly affected by the bandwidth of the transmit signal. When a sampling gate is smaller, the transmit signal is shorter, the bandwidth is wider, and thus the Doppler spectral resolution is poorer. In addition, in the scatterers with the same reflected energy at different velocities, fast scatterers move out of the sampling volume earlier, so that for a certain period of time (N pulse repetition time (PRT)), the fast scatterer has fewer reflected signals. While the conventional method of acquiring a sampling signal by performing simple averaging or difference on the signals in the sampling gate greatly weakens the energy of the high-velocity blood flow, so that the energy of a final velocity spectrum is not uniform.

SUMMARY

The thoughts regarding the present invention are to provide a pulsed Doppler ultra-high spectral resolution imaging processing method and processing system.

In order to realize one of the above thoughts, a pulsed Doppler ultra-high spectral resolution imaging processing method is provided according to an embodiment of the present invention, and comprises the following steps: S1, acquiring IQ signals corresponding to N sampling points on each scan line to form an IQ signal sequence corresponding to each scan line; in a fast time direction, performing wall filtering processing on the IQ signal sequence corresponding to each scan line to form an IQ signal wall filtering sequence corresponding to each scan line; S2, performing Fast Fourier Transformation (FFT) on each sampling point in the IQ signal wall filtering sequence in a slow time direction and the fast time direction, respectively, to obtain an energy distribution matrix of each sampling point at different frequency shifts; S3, acquiring, according to a frequency shift coordinate value of each sampling point in the energy distribution matrix, a pulse repetition frequency of an initial transmit signal, and a center frequency of the initial transmit signal, a velocity distribution matrix of each sampling point matching the energy distribution matrix at the different frequency shifts; and S4, retrieving a velocity sequence for display, querying the velocity distribution matrix and the energy distribution matrix matching the velocity matrix according to the velocity sequence, and acquiring an energy sequence corresponding to the velocity sequence for displaying a final spectrum.

As an improvement of an embodiment of the present invention, the step S1 further comprises: presetting M storage spaces, each storage space storing a set of IQ signal sequences, and sequentially storing the signal sequences in a first-in-first-out manner to obtain M sets of IQ signal sequences; and performing wall filtering processing on the M sets of IQ signal sequences to form an M*N data matrix for sequentially performing FFT in the slow time direction and the fast time direction.

As a further improvement of an embodiment of the present invention, the step S2 particularly comprises: P1, sequentially performing windowing and 2D-FFT on the M*N data matrix, and acquiring a modulus square of a complex number of each data point in the M*N data matrix to form an initial energy distribution matrix of M*N; and P2, transposing the initial energy distribution matrix of M*N to form an energy distribution matrix of N*M.

As a further improvement of an embodiment of the present invention, the step S3 particularly comprises: acquiring a velocity distribution matrix of N*M composed of V_Matrix(x, y); when fsig(j)<B_iq and fsig(j)>−B_iq, V_Matrix(i,j)=fd(i)*c/(2*(fsig(j)+f0)), otherwise V_Matrix(i,j)=−Prf*c/(2*f0), wherein V_Matrix(x, y) represents a velocity with a frequency shift of fd(x)=x/(N−1)*Prf and a corresponding frequency component of fsig(y)=y/(M−1)*fs-fs/2; B_iq represents a bandwidth of a wall filter during the wall filtering process of the IQ signal sequence; Prf is the pulse repetition frequency of the initial transmit signal; f0 is the center frequency of the initial transmit signal; c is a propagation velocity of ultrasound within a tissue; and fs is a signal sampling frequency.

As a further improvement of an embodiment of the present invention, the step S4 specifically comprises: M1, initializing an initial energy value and an initial number of sampling, points corresponding to each data point in the velocity sequence for display to 0; M2, sequentially querying the velocity distribution matrix with each data point in the velocity sequence for display, acquiring an accumulative coefficient according to a predetermined rule depending on a velocity of each data point in the velocity sequence for display, the size of each matrix velocity point in the velocity distribution matrix and coordinate values of each matrix velocity point, and acquiring a matrix energy value corresponding to each accumulative coefficient in the energy distribution matrix; and M3, acquiring, according to the matrix energy value obtained for each data point in the velocity sequence for display and the accumulative coefficient, a total energy value corresponding to each data point in the velocity sequence for display to form an energy sequence corresponding to the velocity sequence for displaying a final spectrum.

In order to realize one of the above thoughts, a pulsed Doppler ultra-high spectral resolution imaging processing system is provided according to an embodiment of the present invention, comprising: a gate sampling module configured to acquire IQ signals corresponding to N sampling points respectively on each scan line to form an IQ signal sequence corresponding to each scan line; a wall filtering processing module configured to perform wall filtering processing on the IQ signal sequence corresponding to each scan line in a fast time direction to form an IQ signal wall filtering sequence corresponding to each scan line; an FFT module configured to perform FFT on each sampling point in the IQ signal wall filtering sequence in a slow time direction and the fast time direction, respectively, to obtain an energy distribution matrix of each sampling point at different frequency shifts; a matrix matching module configured to acquire, according to frequency shift coordinate values of each sampling point in the energy distribution matrix, a pulse repetition frequency of an initial transmit signal, and a center frequency of the initial transmit signal, a velocity distribution matrix of each sampling point matching the energy distribution matrix at the different frequency shifts; and a processing output module configured to retrieve a velocity sequence for display, query the velocity distribution matrix and the energy distribution matrix matching the velocity matrix with the velocity sequence, and acquire an energy sequence corresponding to the velocity sequence for displaying a final spectrum.

As a further improvement of an embodiment of the present invention, M storage spaces are preset, each storage space stores a set of IQ signal sequences, and the gate sampling module sequentially stores the signal sequences in a first-in-first-out manner to obtain M sets of IQ signal sequences; and after the wall filtering processing module performs wall filtering processing on the M sets of IQ signal sequences, an M*N data matrix is formed for sequentially performing FFT in the slow time direction and the fast time direction.

As a further improvement of an embodiment of the present invention, the FFT module is particularly configured to: sequentially perform windowing and 2D-FFT on the M*N data matrix, acquire a modulus square of a complex number of each data point in the M*N data matrix to form an initial energy distribution matrix of M*N, and transpose the initial energy distribution matrix of M*N to form an energy distribution matrix of N*M.

As a further improvement of an embodiment of the present invention, the matrix matching module is particularly configured to: acquire a velocity distribution matrix of N*M composed of V_Matrix(x, y); when fsig(j)<B_iq and fsig(j)>−B_iq, V_Matrix(i,j)=fd(i)*c/(2*(fsig(j)+f0)), otherwise V_Matrix(i,j)=−Prf*c/(2*f0)), wherein V_Matrix(x, y) represents a velocity with a frequency shift of fd(x)=x/(N−1)*Prf, and a corresponding frequency component of fsig (y)=y/(M−1)*fs-fs/2; B_iq represents a bandwidth of a wall filter during the wall filtering process of the IQ signal sequence; Prf is the pulse repetition frequency of the initial transmit signal; f0 is the center frequency of the initial transmit signal; c is a propagation velocity of ultrasound within a tissue; and fs is a signal sampling frequency.

As a further improvement of an embodiment of the present invention, the processing output module is particularly configured to: M1, initials an initial energy value and an initial number of sampling points corresponding to each data point in the velocity sequence for display to 0; M2, sequentially query the velocity distribution matrix with each data point in the velocity sequence for display, acquire an accumulative coefficient according to a predetermined rule depending on a velocity of each data point in the velocity sequence for display, the size of each matrix velocity point in the velocity distribution matrix, coordinate values of each matrix velocity point, and acquire a matrix energy value corresponding to each accumulative coefficient in the energy distribution matrix; and M3, acquire, according to the matrix energy value obtained for each data point in the velocity sequence for display and the accumulative coefficient, a total energy value corresponding to each data point in the velocity sequence for display to form an energy sequence corresponding to the velocity sequence for displaying, a final spectrum.

Compared with the prior art, according to the pulse Doppler ultra-high spectral resolution imaging processing method and processing system of the present invention, two-dimensional fast Fourier transform is performed after performing wall filtering on an IQ signal sequence; then, a corresponding energy distribution matrix and velocity distribution matrix within art effective bandwidth of an IQ signal are acquired according to a frequency shift and a fast time frequency component of the signal; and finally, according to a velocity scale for display, the energy distribution matrix and the velocity distribution matrix are queried, and a corresponding energy sequence for display and imaging is acquired. In the present invention, when the transmit signal bandwidth is wider or the scatterer velocity is faster, the velocity resolution is greatly guaranteed, the velocity spectrum resolution is greatly improved, and the signal-to-noise ratio is also improved, thereby improving the convenience and efficiency of an ultrasound imaging device and enhancing the quality of an ultrasound image.

DETAILED DESCRIPTION

The present invention will be described in detail below in conjunction with the embodiments shown in the drawings. However, these embodiments are not intended to limit the present invention, and changes in the structures, methods or functions made by those skilled in the art in accordance with the embodiments are included in the protective scope of the present invention.

It should be noted that the present invention is mainly applied to an ultrasonic device. Accordingly, an object to be tested may be a tissue to be tested, which will not be described in detail herein.

Figure 1:
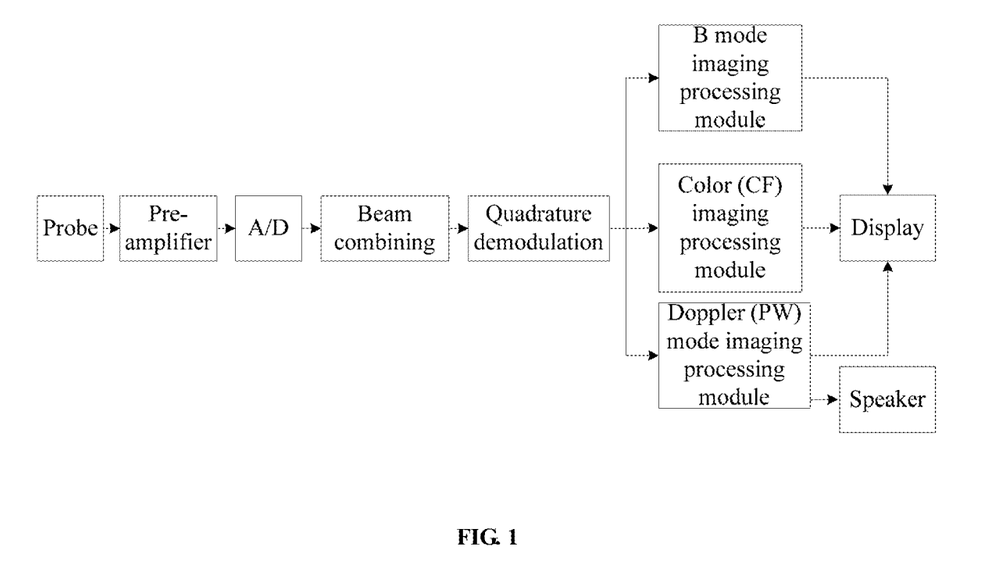
FIG. 1 is an overall block diagram of a conventional imaging system.

Combined with FIG. 1, a block diagram of a Doppler imaging system is shown.

During pulsed Doppler ultra-high spectral resolution imaging, a pulse signal is transmitted to a tissue through a probe. The pulse signal is reflected by the tissue to form an ultrasonic signal, which is converted into an electrical analog signal by different primitives of a probe transducer; and the electrical analog signal is amplified by a preamplifier module, and then is converted by an A/D digital-to-analog module into a digital signal. The digital signals of different primitives are combined into a radio frequency signal through a beam combining module. After the radio frequency signal is subjected to quadrature demodulation at a fixed frequency, a quadrature demodulation resulting I/Q signal is sent to a corresponding processing module.

In the above-mentioned pulsed Doppler ultra-high spectral resolution imaging process, a pulse repetition frequency (PRF) and a transmit center frequency f0 of the transmit pulse signal are system preset values. In the beam combining process of the digital signal, quadrature demodulation needs to be done through a low-pass filter. A demodulation bandwidth B_iq of the low pass filter is also a system preset threshold.

Figure 2:
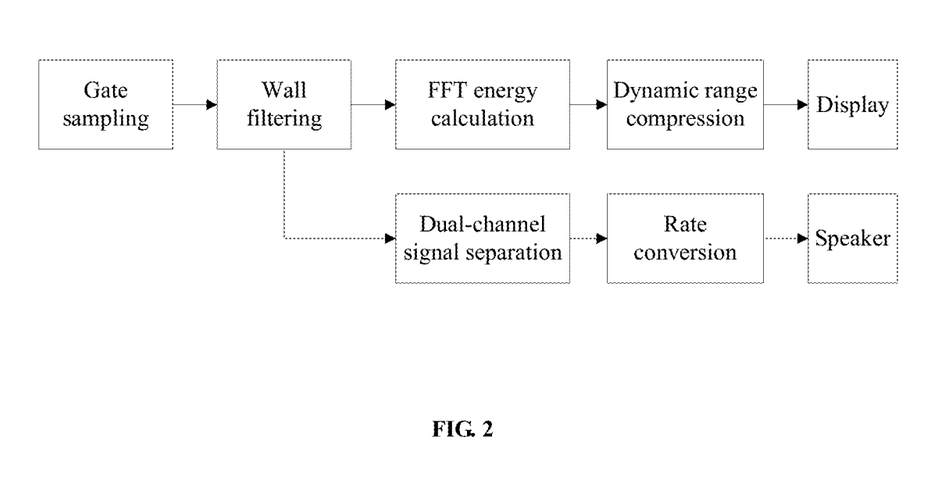
FIG. 2 is a block diagram of a conventional pulsed Doppler ultra-high spectral resolution imaging processing system.

As shown in FIG. 2, the conventional pulsed Doppler (PW) mode imaging requires the following process.

In a gate sampling module, signal sampling points in a sampling gate are intercepted, and all the intercepted sampling points are averaged and then are sent to a wall filtering module. The wall filtering module is generally a high-pass filter, which is mainly used for filtering a tissue signal of low-velocity motion in the signals in a slow time direction. The conventional methods, a low-order FIR filter, an IIR filter, and a polynomial regression filter are used. Among these filters, the projection-initialized IIR filter and the polynomial regression filter have the performance advantages of large stop-band attenuation, narrow transition band, no data loss, and the like. The stop-band cutoff frequency of the projection-initialized IIR filter is more flexible. The signal subjected to wall filtering is sent to a subsequent FFT energy calculation module and a two-channel separation module.

The FFT energy calculation module performs fast Fourier transform (FFT) on the signal subjected to wall filtering to obtain an energy magnitude of each frequency-shift component, then performs logarithmic compression through a dynamic range compression nodule, and finally displays a spectrum.

The two-channel separation module mainly separates positive and negative spectrums of a signal into left and right channels, then converts the separated spectrums into a sampling rate required by a system sound card by means of rate conversion, and finally performs audio playback.

Figure 3:
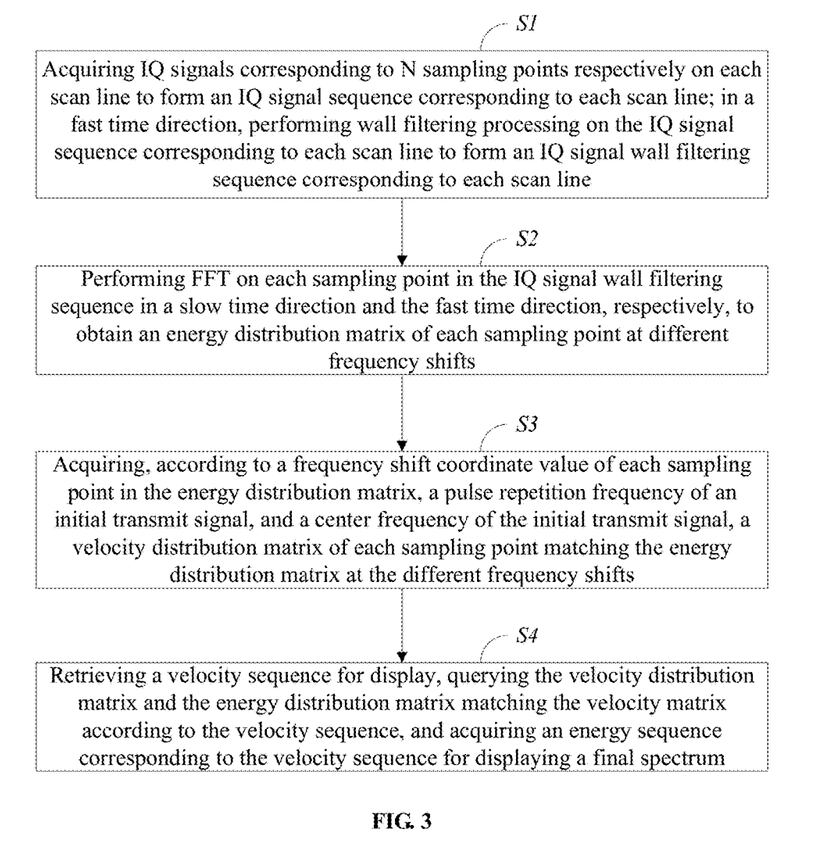
FIG. 3 is a schematic flow chart of a pulsed Doppler ultra-high spectral resolution imaging processing method according to an embodiment of the present invention.

As shown in FIG. 3, FIG. 3 is a flow chart of a pulsed Doppler ultra-high spectral resolution imaging processing method according to an embodiment of the present invention. The method includes: S1, acquiring IQ signals corresponding to N sampling points respectively on each scan line to form an IQ signal sequence corresponding to each scan line; and in a fast time direction, performing wall filtering processing on the IQ signal sequence corresponding to each scan line to form an IQ signal wall filtering sequence corresponding to each scan line.

In a specific example of the present invention, for convenience of description, coordinate points corresponding to N sampling points respectively on each echo signal are represented by (x, y).

Typically, sampling is performed on a corresponding echo signal based on the size of the sampling gate, the sampling gate size being expressed in SV.

Accordingly, for the i-th scan line, i is a positive integer, and the corresponding IQ signal wall filtering sequence can be expressed as:

$$\{IQ(1,i), IQ(2,i), IQ(3,i), \ldots IQ(N,i)\}.$$

$N=2*SV/c*fs$, c is a propagation velocity of ultrasound in a tissue, and fs is a signal sampling frequency.

Further, in a preferred embodiment of the present invention, the step S1 further includes: presetting M storage spaces, each storage space storing a set of IQ signal sequences, and sequentially storing the signal sequences in a first-in-first-out manner to obtain M sets of IQ signal sequences; and performing wall filtering processing on the M sets of IQ signal sequences to form an M*N data matrix for sequentially performing FFT in the slow time direction and the fast time direction.

After all the M storage spaces store data, the next IQ signal sequence needs to wait before storing till the output or removal of the IQ signal sequence in the most front storage space is completed.

In a specific implementation of the present invention, after performing wall faltering processing on the M sets of IQ signal sequences, the M*N data matrix is composed of:

$$\{IQ(1, i), IQ(2, i), IQ(3, i), \ldots, IQ(N, i)\};$$

$$\{IQ(1, i+1), IQ(2, i+1), IQ(3, i+1), \ldots, IQ(N, i+1)\};$$

$$\{IQ(1, i+2), IQ(2, i+2), IQ(3, i+2), \ldots, IQ(N, i+2)\};$$

$$\ldots ; \text{and}$$

$$\{IQ(1, i+M-1), IQ(2, i+M-1), IQ(3, i+M-1), \ldots, IQ(N, i+M-1)\}.$$

It should be noted that, in other embodiments of the present invention, all the acquired wall filtering signal sequences may be used for subsequent calculation, which will not be described in detail herein.

In an embodiment of the invention, the method further includes: S2, performing FFT on each sampling point in the IQ signal wall filtering sequence in the slow time direction and the fast time direction, respectively, to obtain an energy distribution matrix of each sampling point at different frequency shifts.

In this embodiment, FFT is sequentially performed on each sampling point in the IQ signal wall filtering sequence in the slow time direction to respectively acquire an energy distribution corresponding to each sampling point in the IQ signal wall filtering sequence at different frequency shifts; and further, FFT is performed in the fast time direction to obtain an energy distribution at different frequency shift components.

In the specific implementation of the present invention, the step S2 particularly includes: P1, sequentially performing windowing and 2D-FFT on the M*N data matrix, and acquiring a modulus square of a complex number of each data point in the M*N data matrix to form an initial energy distribution matrix of M*N.

Accordingly, the formed initial energy distribution matrix of M*N is:

{P_2DFFT(1, $i$), P_2DFFT(2, $i$), P_2DFFT(3, $i$), ... ,

P_2DFFT($N$, $i$)};

{P_2DFFT(1, $i+1$), P_2DFFT(2, $i+1$), P_2DFFT(3, $i+1$),

... , P_2DFFT($N$, $i+1$)};

{P_2DFFT(1, $i+2$), P_2DFFT(2, $i+2$), P_2DFFT(3, $i+2$),

... , P_2DFFT($N$, $i+2$)};

... ; and

{P_2DFFT(1, $i+M-1$), P_2DFFT(2, $i+M-1$),

P_2DFFT(3, $i+M-1$), ... , P_2DFFT($N$, $i+M-1$)}.

Further, the step S2 further includes: P2, transposing the initial energy distribution matrix of M*N to form an energy distribution matrix of N*M.

{P_2DFFT(1, $i$), P_2DFFT(1, $i+1$), P_2DFFT(1, $i+2$), ... ,

P_2DFFT(1, $i+M-1$)};

{P_2DFFT(2, $i$), P_2DFFT(2, $i+1$), P_2DFFT(2, $i+2$),

... , P_2DFFT(2, $i+M-1$)};

{P_2DFFT(3, $i$), P_2DFFT(3, $i+1$), P_2DFFT(3, $i+2$),

... , P_2DFFT(3, $i+M-1$)};

... ; and

{P_2DFFT($N$, $i$), P_2DFFT($N$, $i+1$), P_2DFFT($N$, $i+2$), ... ,

P_2DFFT($N$, $i+M-1$)}.

Further, in an embodiment of the present invention, the method further includes: S3, acquiring, according to a frequency shift coordinate value of each sampling point in the energy distribution matrix, a pulse repetition frequency of an initial transmit signal, and a center frequency of the initial transmit signal, a velocity distribution matrix of each sampling point matching the energy distribution matrix at the different frequency shifts.

In a specific example of the present invention, the step S3 particularly includes: acquiring a velocity distribution matrix of N*M composed of V_Matrix(x, y).

The velocity distribution matrix matching the energy distribution matrix of N*M is:

{V_MATRIX(1, $i$), V_MATRIX(1, $i+1$),

V_MATRIX(1, $i+2$), ... , V_MATRIX(1, $i+M-1$)};

{V_MATRIX(2, $i$), V_MATRIX(2, $i+1$),

V_MATRIX(2, $i+2$), ... , V_MATRIX(2, $i+M-1$)};

{V_MATRIX(3, $i$), V_MATRIX(3, $i+1$),

V_MATRIX(3, $i+2$), ... , V_MATRIX(3, $i+M-1$)};

... ; and

{V_MATRIX($N$, $i$), V_MATRIX($N$, $i+1$),

V_MATRIX($N$, $i+2$), ... , V_MATRIX($N$, $i+M-1$)}.

When fsig($j$)<$B\_iq$ and fsig($j$)>−$B\_iq$, $V\_Matrix(i,j)=fd(i)*c/(2*(fsig(j)+f0))$, otherwise $V\_Matrix(i,j)=-Prf*c/(2*f0))$, wherein V_Matrix(x, y) represents a velocity with a frequency shift of fd(x)=x/(N−1)*Prf and a corresponding frequency component of fsig(y)=y/(M−1)*fs-fs/2; B_iq represents a bandwidth of a wall filter during the wall filtering process of the IQ signal sequence; Prf is the pulse repetition frequency of the initial transmit signal; f0 is the center frequency of the initial transmit signal; c is a propagation velocity of ultrasound within a tissue; and fs is a signal sampling frequency.

According to the above formula, the size of each data point in the velocity distribution matrix is related to the parameters M, N, fs and Prf, wherein M and fs are constants in the system. Thus, only when the sampling gate size or the pulse repetition frequency of the initial transmit signal changes, the size of each data point in the velocity distribution matrix changes accordingly, which will not be described in detail herein.

Further, in an embodiment of the invention, the method further includes: S4, retrieving a velocity sequence for display, querying the velocity distribution matrix and the energy distribution matrix matching the velocity matrix according to the velocity sequence, and acquiring an energy sequence corresponding to the velocity sequence for displaying a final spectrum.

The velocity sequence for display can be obtained in the following manner. In the pulsed Doppler scan, the maximum display velocity is expressed by V_max, and the velocity sequence for display is represented by V_Dis.

Then, each data in the velocity sequence for display is $V\_Dis(j)=j*V\_max/K, j=(0,1, ... K-1)$, and $V\_max=Prf*c/(2*f0)$, K is a system set parameter, can be set according to the need, and thus will not be described in detail here.

In a specific example of the present invention, the step S4 particularly includes: M1, initializing an initial energy value and an initial number of sampling points corresponding to each data point in the velocity sequence for display to 0; M2, sequentially querying the velocity distribution matrix with each data point in the velocity sequence for display, acquiring an accumulative coefficient according to a predetermined rule depending on a velocity of each data point in the velocity sequence for display, the size of each matrix velocity point in the velocity distribution matrix and coordinate values of each matrix velocity point, and acquiring a matrix energy value corresponding to each accumulative coefficient in the energy distribution matrix; and M3, acquiring, according to the matrix energy value obtained for each data point in the velocity sequence for display and the accumulative coefficient, a total energy value corresponding to each data point in the velocity sequence for display to form an energy sequence corresponding to the velocity sequence for displaying a final spectrum.

In a specific example of the present invention, the energy value is represented by Power_V(j), and the number of sampling points is represented by V_Num(j).

After initialization, the initial energy value corresponding to each data point Power_V(0)=0, and an initial number of sampling points V_Num(j)=0.

Each row of the velocity distribution matrix is sequentially queried with the data point V_Dis(j) until a first matrix velocity value V_Matrix(n_v, m_v) greater than or equal to the data point V_Dis(j) in the current row is obtained.

Certainly, if there is no matrix velocity value V_Matrix(n_v, m_v) greater than or equal to the data point V_Dis(j) in the current row after the query, the energy value of a V_Dis(j) corresponding to the current row is 0, and the next row of the velocity distribution matrix is queried continuously.

If the value of the data point V_Dis(j) is equal to the matrix velocity value V_Matrix(n_v, m_v) in the current row, the matrix energy value corresponding to the coordinate values of (n_v, m_v) in the energy distribution matrix is directly used as the energy value of the data point V_Dis(j) in the current row.

If the velocity value V_Matrix(n_v, m_v) in the current row is greater than the value of the data point V_Dis(j) after the query, an accumulative coefficient of V_Dis(j) is obtained by using a predetermined rule.

The predetermined rule is, for example, an interpolation method, an absolute value method, a cubic method, or the like.

For ease of understanding, the present invention only introduces the interpolation method as an example.

In this specific example, only one row of data points of the velocity distribution matrix is queried for specific description.

For a certain row of the velocity matrix:

$c1 = Dis\_b^2 / (Dis\_a^2 + Dis\_b^2);$ $c2 = 1 - c1;$ $Dis\_a = V\_Dis(i) - V\_Matrix(n\_v, m\_v - 1);$ and $Dis\_b = V\_Matrix(n\_v, m\_v) - V\_Dis(i),$ wherein c1 and c2 represent accumulative coefficients corresponding to coordinate points (n_v, m_v−1) and (n_v, m_v), respectively.

Further, according to the matrix energy value in the energy distribution matrix corresponding to the coordinate point obtained in each row and the accumulative coefficient thereof, an energy value corresponding to each data point in each row is obtained, and the energy value obtained for each row is accumulated to form an accumulative energy value corresponding to the current data point.

$\Sigma Power\_V(i) = Power\_V(0) + c1*P\_2DFFT(n\_v, m\_v-1) + c2*P\_2DFFT(n\_v, m\_v) + \ldots$ Power_V(0) represents the initial energy value of the data point, and ΣPower_V(i) represents the accumulative energy value corresponding to the data point.

Further, the total energy value corresponding to each data point is

Power_V(i)=ΣPower_V(i)ΣV_Num(i), wherein Power_V(i) represents the total energy value, and ΣV_Num(i) represents the number of matrix energy values participating in the calculation.

Of course, in other embodiments of the present invention, an average value, a maximum value, a maximum value, a side value, and a median value of a plurality of matrix energy values in the energy distribution matrix corresponding to the data point V_Dis(j) may be used as the total energy corresponding to each data point V_Dis(j), which will not described in detail herein.

Further, an energy sequence formed by the total energy value corresponding to each data point V_Dis(j) is subjected to dynamic range compression, and finally is output for display, which will not be described in detail herein.

Figure 5A:
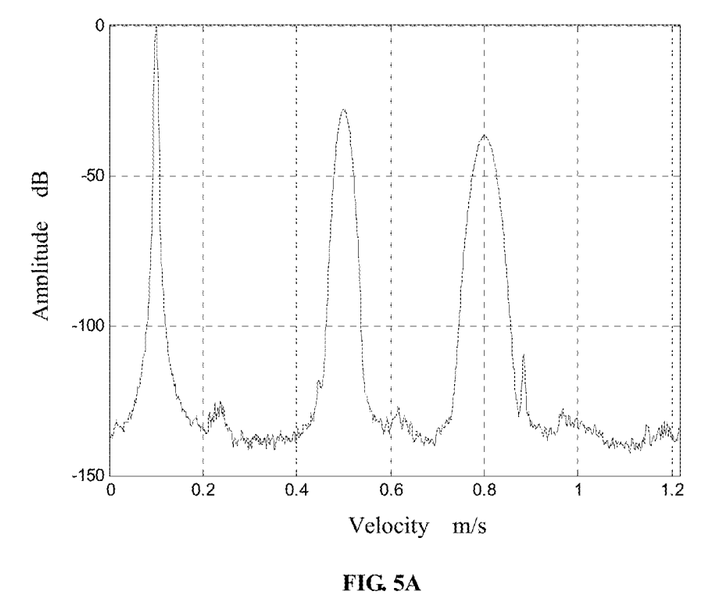
FIGS. 5A and 5B are comparison diagrams of velocity spectra obtained by using a conventional pulsed Doppler ultra-high spectral resolution imaging processing method and a pulsed Doppler ultra-high spectral resolution imaging processing method of the present invention, respectively, in a specific example of the present invention.
Figure 5B:
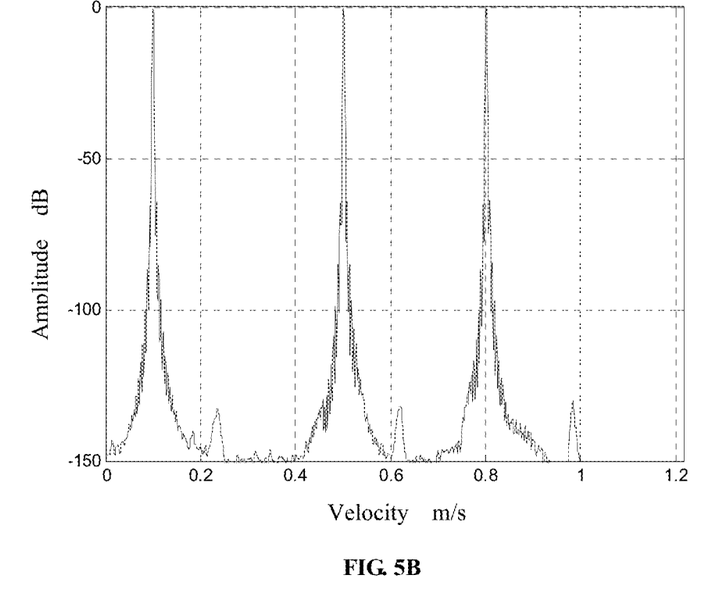
Figure 5C:
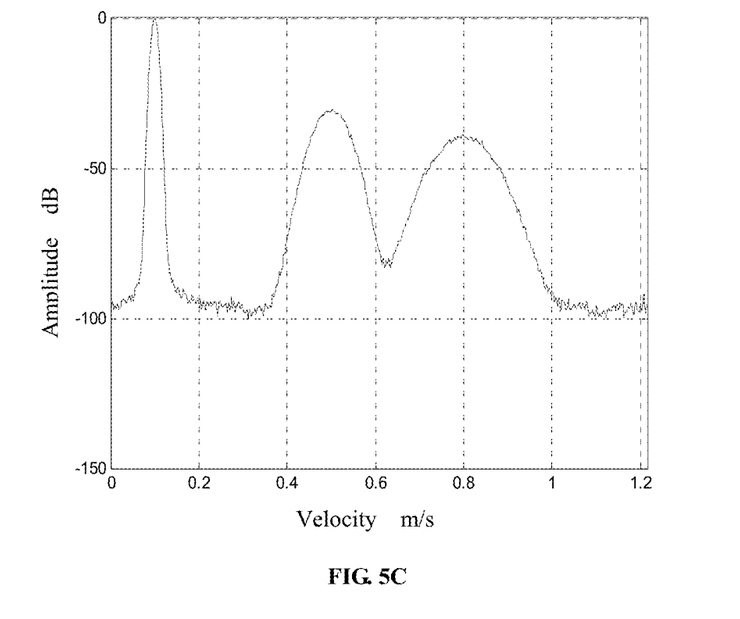
FIG. 5C and FIG. 5D are comparison diagrams of velocity spectra obtained by using a conventional pulsed Doppler ultra-high spectral resolution imaging processing method and a pulsed Doppler ultra-high spectral resolution imaging processing method of the present invention, respectively, in another specific example of the present invention.
Figure 5D:
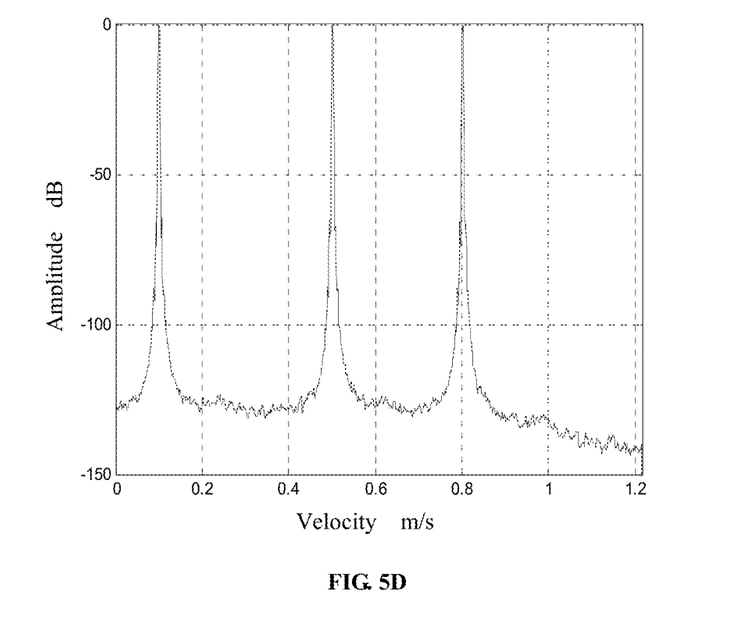

As shown in FIGS. 5A-5D, FIG. 5A is a velocity spectrum obtained by a conventional pulsed Doppler ultrahigh spectral resolution imaging processing method under Condition 1; and FIG. 5B is a velocity spectrum obtained by a pulsed Doppler ultrahigh spectral resolution imaging processing method according to the present invention under Condition 1. FIG. 5C is a velocity spectrum obtained by a conventional pulsed Doppler ultra-high spectral resolution imaging processing method under Condition 2; and FIG. 5D is a velocity spectrum obtained by a pulsed Doppler ultra-high spectral resolution imaging processing method according to the present invention under Condition 2.

In FIG. 5A and FIG. 5B, the center frequency of the initial transmit signal is 5 MHz; the number of transmit periods is 20; the pulse repetition frequency of the initial transmit signal is 8 kHz; three scatterer velocities are respectively 0.1 m/s, 0.5 m/s and 0.8 m/s; and the random noise level is −20 dB.

In FIG. 5C and FIG. 5D, the center frequency of the initial transmit signal is 5 MHz; the number of transmit periods is 6; the pulse repetition frequency of the initial transmit signal is 8 KHz; three scatterer velocities are respectively 0.1 m/s, 0.5 m/s and 0.8 m/s; and the random noise level is −20 dB.

By analyzing the velocity spectrum of FIG. 5A, it can be concluded that the scatterer velocity spectrum resolution gradually deteriorates with the increase of the velocity, and the energy amplitude also gradually decreases at the same time.

By analyzing the velocity spectra of FIGS. 5A and 5C, it can be concluded that the velocity spectrum resolution of the conventional processing method decreases as the bandwidth of the transmit signal is wider.

By analyzing the velocity spectra of FIGS. 5A and 5B it can be concluded that the velocity spectrum resolution of the present invention is greatly improved and is not affected by the scatterer velocity.

By analyzing the velocity spectra of FIGS. 5C and 5D, it can be concluded that the velocity spectrum resolution of the present invention is greatly improved and is not affected by the bandwidth of the transmit signal at the same time; and meanwhile, the problem of the spectrum energy noel-uniformity is also solved, and the signal-to-noise ratio is also improved.

By analyzing the velocity spectra of FIGS. 5B and 5D, it can be concluded that the velocity spectrum resolution is basically the same in the case where the transmit bandwidth is different.

Figure 4:
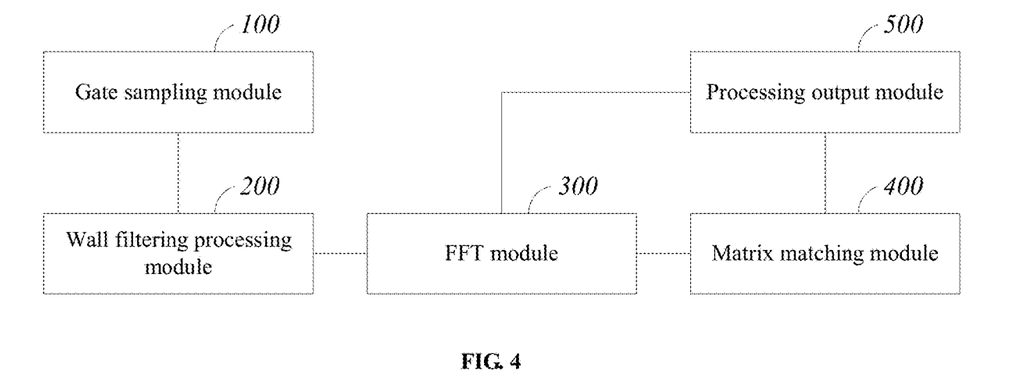
FIG. 4 is a block diagram showing a pulsed Doppler ultra-high spectral resolution imaging processing system according to an embodiment of the present invention.

As shown in FIG. 4, a pulsed Doppler ultra-high spectral resolution imaging processing system provided in an embodiment of the present invention includes: a gate sampling module 100, a wall filtering processing module 200, an FFT module 300, a matrix matching module 400, and a processing output module 500.

The gate sampling module 100 is configured to acquire IQ signals corresponding to N sampling points respectively on each scan line to form an IQ signal sequence corresponding to each scan line.

The wall filtering processing nodule 200 is configured to perform wall filtering processing on the IQ signal sequence corresponding to each scan line in a fast time direction to form an IQ signal wall filtering sequence corresponding to each scan line.

In a specific example of the present invention, for convenience of description, coordinate points corresponding to N sampling points respectively on each echo signal are represented by (x, y).

Typically, the gate sampling module 100 samples on the corresponding echo signal based on the size of the sampling gate, the sampling gate size being represented by SV.

Accordingly, for the i-th scan line, i is a positive integer, and the corresponding IQ signal wall filtering sequence can be expressed as:

{IQ(1,i),IQ(2,i),IQ(3,i), ... IQ(N,i)}.

N=2*SV/c*fs; c is a propagation velocity of ultrasound in a tissue; and fs is a signal sampling frequency.

Further, in a preferred embodiment of the present invention, the step S1 further includes: presetting M storage spaces, each storage space storing a set of IQ signal sequences; sequentially storing the signal sequences by the gate sampling module 100 in a first-in-first-out manner to obtain M sets of IQ signal sequences; and performing wall filtering processing on the M sets of IQ signal sequences by the wall filtering processing module 200 to form an M*N data matrix for sequentially performing FFT in a slow time direction and the fast time direction.

After all the M storage spaces store data, the next IQ signal sequence needs to wait before storing till the output or removal of the IQ signal sequence in the most front storage space is completed.

In the specific implementation of the present invention, after the wall filtering processing module 200 performs wall filtering processing on the M sets of IQ signal sequences, the M*N data matrix is composed of:

{IQ(1, i), IQ(2, i), IQ(3, i), ... , IQ(N, i)};

{IQ(1, i + 1), IQ(2, i + 1), IQ(3, i + 1), ... , IQ(N, i + 1)};

{IQ(1, i + 2), IQ(2, i + 2), IQ(3, i + 2), ... , IQ(N, i + 2)};

... ; and

{IQ(1, i + M − 1), IQ(2, i + M − 1), IQ(3, i + M − 1), ... , IQ(N, i + M − 1)}.

It should be noted that, in other embodiments of the present invention, all the acquired wall filtering signal sequences may be used for subsequent calculation, which will not be described in detail herein.

In an embodiment of the present invention, the FFT module 300 is configured to perform FFT on each sampling point in the IQ signal wall filtering sequence in the slow time direction and the fast time direction, respectively, to obtain an energy distribution matrix of each sampling point at different frequency shifts.

In this embodiment, the FFT module 300 is configured to perform FFT on each sampling point in the IQ signal wall filtering sequence in the slow time direction, respectively, to acquire an energy distribution of each sampling, point in the IQ signal wall filtering sequence at different frequency shifts. Further, the FFT module 300 is configured to perform FFT in the fast time direction to obtain an energy distribution at different frequency shift components.

In a specific embodiment of the present invention, the FFT module 300 is configured to sequentially perform windowing and 2D-FFT on the M*N data matrix, and acquire a modulus square of a complex number of each data point in the M*N data matrix to form an initial energy distribution matrix of M*N.

Accordingly, the formed initial energy distribution matrix of N is:

{P_2DFFT(1, i), P_2DFFT(2, i), P_2DFFT(3, i), ... ,

P_2DFFT(N, i)};

{P_2DFFT(1, i + 1), P_2DFFT(2, i + 1), P_2DFFT(3, i + 1),

... , P_2DFFT(N, i + 1)};

{P_2DFFT(1, i + 2), P_2DFFT(2, i + 2), P_2DFFT(3, i + 2),

... , P_2DFFT(N, i + 2)};

... ; and

{P_2DFFT(1, i + M − 1), P_2DFFT(2, i + M − 1),

P_2DFFT(3, i + M − 1), ... , P_2DFFT(N, i + M − 1)}.

Further, the FFT module 300 is further configured to transpose the initial energy distribution matrix of M*N to form an energy distribution matrix of N*M.

{P_2DFFT(1, i), P_2DFFT(1, i + 1), P_2DFFT(1, i + 2), ... ,

P_2DFFT(1, i + M − 1)};

{P_2DFFT(2, i), P_2DFFT(2, i + 1), P_2DFFT(2, i + 2),

... , P_2DFFT(2, i + M − 1)};

{P_2DFFT(3, i), P_2DFFT(3, i + 1), P_2DFFT(3, i + 2),

... , P_2DFFT(3, i + M − 1)};

... ; and

{P_2DFFT(N, i), P_2DFFT(N, i + 1), P_2DFFT(N, i + 2), ... ,

P_2DFFT(N, i + M − 1)}.

Further, in an embodiment of the present invention, the matrix matching module 400 is configured to: acquire, according to a frequency shift coordinate value of each sampling point in the energy distribution matrix, a pulse repetition frequency of an initial transmit signal, and a center frequency of the initial transmit signal, a velocity distribution matrix of each sampling point matching the energy distribution matrix at the different frequency shifts.

In a specific example of the present invention, the matrix matching module 400 is configured to: acquire a velocity distribution matrix of N*M composed of V_Matrix(x, y). The velocity distribution matrix matching the energy distribution matrix of N*M is:

$\{V\_MATRIX(1, i), V\_MATRIX(1, i+1),$ $V\_MATRIX(1, i+2), \ldots, V\_MATRIX(1, i+M-1)\};$ $\{V\_MATRIX(2, i), V\_MATRIX(2, i+1),$ $V\_MATRIX(2, i+2), \ldots, V\_MATRIX(2, i+M-1)\};$ $\{V\_MATRIX(3, i), V\_MATRIX(3, i+1),$ $V\_MATRIX(3, i+2), \ldots, V\_MATRIX(3, i+M-1)\};$ $\ldots$ ; and $\{V\_MATRIX(N, i), V\_MATRIX(N, i+1),$ $V\_MATRIX(N, i+2), \ldots, V\_MATRIX(N, i+M-1)\}.$ When $fsig(j) < B\_iq$ and $fsig(j) > -B\_iq$, $V\_Matrix(i,j) = fd(i)*c/(2*(fsig(j)+f0));$ otherwise $V\_Matrix(i,j) = -Prf*c/(2*f0)).$ V_Matrix(x, y) represents a velocity with a frequency shift of $fd(x)=x/(N-1)*Prf$, and a corresponding frequency component of $fsig(y)=y/(M-1)*fs-fs/2$; B_iq represents a bandwidth of a wall filter during the wall filtering process of the IQ signal sequence; Prf is the pulse repetition frequency of the initial transmit signal; f0 is the center frequency of the initial transmit signal; c is a propagation velocity of ultrasound within a tissue; and fs is a signal sampling frequency.

According to the above formula, the size of each data point in the velocity distribution matrix is related to the parameters M, N, fs and Prf, wherein M and fs are constants in the system. Thus, only when the sampling gate size or the pulse repetition frequency of the initial transmit signal changes, the size of each data point in the velocity distribution matrix changes accordingly, which will not be described in detail herein.

Further, in an embodiment of the present invention, the processing output module 500 is configured to: retrieve a velocity sequence for display, query the velocity distribution matrix and the energy distribution matrix matching the velocity matrix with the velocity sequence, and acquire an energy sequence corresponding to the velocity sequence for displaying a final spectrum.

The velocity sequence for display can be obtained in the following manner. In the pulsed Doppler scan, the maximum display velocity is expressed by V_max, and the velocity sequence for display is represented by V_Dis.

Then, each data in the velocity sequence for display is $V\_Dis(j) = j*V_{13} max/K, j = (0, 1, \ldots K-1)$
$V\_max = Prf*c/(2*f0).$ K is a system set parameter, which can be set according to the need, and will not be described in detail herein.

In a specific example of the present invention, the processing output module 500 is configured to: initialize an initial energy value and an initial number of sampling points corresponding to each data point in the velocity sequence for display to 0; sequentially query the velocity distribution matrix with each data point in the velocity sequence for display, acquire an accumulative coefficient according to a predetermined rule depending on a velocity of each data point in the velocity sequence for display, the size of each matrix velocity point in the velocity distribution matrix, coordinate values of each matrix velocity point, and acquire a matrix energy value corresponding to each accumulative coefficient in the energy distribution matrix; and acquire, according to the matrix energy value obtained, for each data point in the velocity sequence for display and the accumulative coefficient, a total energy value corresponding to each data point in the velocity sequence for display to form an energy sequence corresponding to the velocity sequence for displaying a final spectrum.

In a specific example of the present invention, the energy value is represented by Power_V(j), and the number of sampling points is represented by V_Num(j).

After initialization, the initial energy value corresponding to each data point Power_V(0)=0, and an initial number of sampling points V_Num(j)=0.

The processing output module 500 sequentially queries each row of the velocity distribution matrix with the data point V_Dis(j) until a first matrix velocity value V_Matrix(n_v, m_v) in the current row greater than or equal to the data point V_Dis(j) is obtained.

Certainly, if there is no matrix velocity value V_Matrix(n_v, m_v) greater than or equal to the data point V_Dis(j) in the current row after the query, the energy value of a V_Dis(j) corresponding to the current row is 0, and the next row of the velocity distribution matrix is queried continuously.

If the value of the data point V_Dis(j) is equal to the matrix velocity value V_Matrix(n_v, m_v) in the current row, the matrix energy value corresponding to the coordinate value of (n_v, m_v) in the energy distribution matrix is directly used as the energy value of the data point V_Dis(j) in the current row.

If the velocity value V_Matrix(n_v, m_v) in the current row is greater than the value of the data point V_Dis(j) after the query, an accumulative coefficient of V_Dis(j) is obtained by using a predetermined rule.

The predetermined rule is, for example, an interpolation method, an absolute value method, a cubic method, or the like.

For ease of understanding, the present invention only introduces the interpolation method as an example.

In this specific example, only one row of data points of the velocity distribution matrix queried by the processing output module 500 is taken as an example.

For a certain row of the velocity matrix:

$c1 = Dis\_b^2/(Dis\_a^2+Dis\_b^2);$ $c2 = 1-c1;$ $Dis\_a = V\_Dis(i) - V\_Matrix(n\_v, m\_v-1);$ and $Dis\_b = V\_Matrix(n\_v, m\_v) - V\_Dis(i).$ c1 and c2 represent accumulative coefficients corresponding to coordinate points (n_v, m_v−1) and (n_v, m_v), respectively.

Further, the processing output module 500 is further configured to: obtain, according to the matrix energy value in the energy distribution matrix corresponding to the coordinate point obtained in each row and the accumulative coefficient thereof, an energy value corresponding to each data point in each row, and accumulate the energy value obtained for each row to form an accumulative energy value corresponding to the current data point.

$\Sigma Power\_V(i) = Power\_V(0) + c1*P\_2DFFT(n\_v, m\_v-1) + c2*P\_2DFFT(n\_v, m\_v) + \ldots$ Power_V(0) represents the initial energy value of the data point; and ΣPower_V(i) represents the accumulative energy value corresponding to the data point.

Further, the total energy value corresponding to each data point is

Power_V(i)=ΣPower_V(i)/ΣV_Num(i), wherein Power_V(i) represents the total energy value; and ΣV_Num(i) represents the number of matrix energy values participating in the calculation.

Of course, in other embodiments of the present invention, an average value, a maximum value, a maximum value, a side value, and a median value of a plurality of matrix energy values in the energy distribution matrix corresponding to the data point V_Dis(j) may be used as the total energy corresponding to each data point V_Dis(i), which will not described in detail herein.

Further, an energy sequence is formed by the total energy value corresponding to each data point V_Dis(j) through the processing output module 500; and the processing output module 500 performs dynamic range compression on this energy sequence, and finally outputs the compressed energy sequence for display, which will not be described in detail herein.

In summary, according to the pulse Doppler ultra-high spectral resolution imaging processing method and processing system of the present invention, two-dimensional fast Fourier transform is performed after performing wall filtering on an IQ signal sequence; then, a corresponding energy distribution matrix and velocity distribution matrix within an effective bandwidth of the IQ signal are acquired according to a frequency shift and a fast time frequency component of the signal: and finally, according to a velocity scale for display, the energy distribution matrix and the velocity distribution matrix are queried, and a corresponding energy sequence for display and imaging is acquired. In the present invention, when the transmit signal bandwidth is wider or the scatterer velocity is faster, the velocity resolution is greatly guaranteed, the velocity spectrum resolution is greatly improved, and the signal-to-noise ratio is also improved, thereby improving the convenience and efficiency of the ultrasound imaging device and enhancing the quality of the ultrasound image.

For the convenience of description, the above device is divided into various modules which are described separately according to functions. Of course, the functions of all modules may be implemented in the same or a plurality of pieces of so are/hardware in the implementation of the present invention.

It will be apparent to those skilled in the art from the above description of the embodiments that the present application can be implemented by means of software with a necessary general hardware platform. Based on this understanding, naturally, the technical solution of the present invention or the contributions to the prior art may be embodied as a software product. The software product may be stored in a storage medium such as a ROM/RAM, a magnetic disk, an optical disc or the like, and may comprise a number of instructions allowing a computer device (which may be a personal computer, an information push server, or a network device, etc.) to perform the methods described in various embodiments of the present embodiments or part of the embodiments.

The device embodiments described above are merely illustrative. The modules described as separate components may or may not be physically separate, and the components displayed as modules may or may not be physical modules, i.e. may be located at the same place, or may also be distributed to a plurality of network modules. Some or all of the modules may be selected according to actual needs to achieve the objects of the technical solution of the present embodiment. Those of ordinary skill in the art can understand and implement the present invention without any creative effort.

The present invention can be described in the general context of computer executable instructions executed by a computer, such as a program module. Generally, program modules include routines, programs, objects, components, data structures, and the like that perform particular tasks or implement particular abstract data types. The present invention may be practiced in distributed computing environments where tasks are performed by remote processing devices that are connected through a communication network. In a distributed computing environment, program modules may be located in local and remote computer storage medium including storage devices.

It should be understood that, although the description is described in terms of embodiments, the embodiments are not intended to merely contain one independent technical solution, and such a narration of the description is merely for the sake of clarity. Those skilled in the art should view the description as a whole. The technical solutions in the embodiments may also be combined as appropriate to form other embodiments that can be understood by those skilled in the art.

The foregoing, detailed description of the preferred embodiments of the present invention is merely a specific description of feasible embodiments of the present invention and is not intended to limit the protective scope of the present invention. All equivalent embodiments or modifications that are made without departing from the spirit of the present invention shall fall within the protective scope of the present invention.

What is claimed is:

1. A pulsed Doppler ultra-high spectral resolution imaging processing method, comprising the steps of:
    S1, acquiring IQ signals corresponding to N sampling points respectively on each scan line to form an IQ signal sequence corresponding to each scan line;
    in a fast time direction, performing wall filtering processing on the IQ signal sequence corresponding to each scan line to form an IQ signal wall filtering sequence corresponding to each scan line;
    S2, performing Fast Fourier Transformation (FFT) on each sampling point in the IQ signal wall filtering sequence in a slow time direction and the fast time direction, respectively, to obtain an energy distribution matrix of each sampling point at different frequency shifts;
    S3, acquiring, according to a frequency shift coordinate value of each sampling point in the energy distribution matrix, a pulse repetition frequency of an initial transmit signal, and a center frequency of the initial transmit signal, a velocity distribution matrix of each sampling point matching the energy distribution matrix at the different frequency shifts; and new line S4, retrieving a velocity sequence for display, querying the velocity distribution matrix and the energy distribution matrix matching the velocity matrix according to the velocity sequence, and acquiring an energy sequence corresponding to the velocity sequence for displaying a final spectrum;
    wherein the step S1 further comprises:
    presetting M storage spaces, each storage space storing a set of IQ signal sequences, and sequentially storing the signal sequences in a first-in-first-out manner to obtain M sets of IQ signal sequences; and new line performing wall filtering processing on the M sets of IQ signal sequences to form an M*N data matrix for sequentially performing FFT in the slow time direction and the fast time direction;

wherein the step S2 comprises:

P1, sequentially performing windowing and 2D-FFT on the M*N data matrix, and acquiring a modulus square of a complex number of each data point in the M*N data matrix to form an initial energy distribution matrix of M*N; and P2, transposing the initial energy distribution matrix of M*N to form an energy distribution matrix of N*M; and wherein the step S3 comprises:

acquiring a velocity distribution matrix of N*M composed of V_Matrix(x, y);

when $fsig(j)<B\_iq$ and $fsig(j)>-B\_iq$, $V\_Matrix(i,j)=fd(i)*c/(2*(fsig(j)+f0))$;

otherwise, $V Matrix(i,j)=-Prf*c/(2*f0))$, wherein

V_Matrix(x, y) represents a velocity with a frequency shift of $fd(x)=x/(N-1)*Prf$ and a corresponding frequency component of $fsig(y)=y/(M-1)*fs-fs/2$; B_iq represents a bandwidth of a wall filter during the wall filtering process of the IQ signal sequence; Prf is the pulse repetition frequency of the initial transmit signal; f0 is the center frequency of the initial transmit signal; c is a propagation velocity of ultrasound within a tissue; and fs is a signal sampling frequency.

2. The pulsed Doppler ultra-high spectral resolution imaging processing method according to claim 1, wherein the step S4 comprises:

M1, initializing an initial energy value and an initial number of sampling points corresponding to each data point in the velocity sequence for display to 0;

M2, sequentially querying the velocity distribution matrix with each data point in the velocity sequence for display, acquiring an accumulative coefficient according to a predetermined rule depending on a velocity of each data point in the velocity sequence for display, the size of each matrix velocity point in the velocity distribution matrix and coordinate values of each matrix velocity point, and acquiring a matrix energy value corresponding to each accumulative coefficient in the energy distribution matrix; and M3, acquiring, according to the matrix energy value obtained for each data point in the velocity sequence for display and the accumulative coefficient, a total energy value corresponding to each data point in the velocity sequence for display to form an energy sequence corresponding to the velocity sequence for displaying a final spectrum.

3. A pulsed Doppler ultra-high spectral resolution imaging processing system, comprising:

a computer device configured to:

acquire IQ signals corresponding to N sampling points respectively on each scan line to form an IQ signal sequence corresponding to each scan line;

perform wall filtering processing on the IQ signal sequence corresponding to each scan line in a fast time direction to form an IQ signal wall filtering sequence corresponding to each scan line;

perform FFT on each sampling point in the IQ signal wall filtering sequence in a slow time direction and the fast time direction, respectively, to obtain an energy distribution matrix of each sampling point at different frequency shifts;

acquire, according to frequency shift coordinate values of each sampling point in the energy distribution matrix, a pulse repetition frequency of an initial transmit signal, and a center frequency of the initial transmit signal, a velocity distribution matrix of each sampling point matching the energy distribution matrix at the different frequency shifts; and retrieve a velocity sequence for display, query the velocity distribution matrix and the energy distribution matrix matching the velocity matrix according to the velocity sequence, and acquire an energy sequence corresponding to the velocity sequence for displaying a final spectrum;

wherein M storage spaces are preset, each storage space stores a set of IQ signal sequences, and the computer device sequentially stores the signal sequences in a first-in-first-out manner to obtain M sets of IQ signal sequences; and after the computer device performs wall filtering processing on the M sets of IQ signal sequences, an M*N data matrix is formed for sequentially performing FFT in the slow time direction and the fast time direction;

wherein the computer device is further configured to:

sequentially perform windowing and 2D-FFT on the M*N data matrix, and acquire a modulus square of a complex number of each data point in the M*N data matrix to form an initial energy distribution matrix of M*N;

transpose the initial energy distribution matrix of M*N to form an energy distribution matrix of N*M; and acquire a velocity distribution matrix of N*M composed of V_Matrix(x, y);

when $fsig(j)<B\_iq$ and $fsig(j)>-B\_iq$, $V\_Matrix(i,j)=fd(i)*c/(2*(fsig(j)+f0))$;

otherwise, $V\_Matrix(i,j)=-Prf*c/(2*f0))$, wherein

V_Matrix(x, y) represents a velocity with a frequency shift of $fd(x)=x/(N-1)*Prf$, and a corresponding frequency component of $fsig(y)=y/(M-1)*fs-fs/2$; B_iq represents a bandwidth of a wall filter during the wall filtering process of the IQ signal sequence; Prf is the pulse repetition frequency of the initial transmit signal; f0 is the center frequency of the initial transmit signal; c is a propagation velocity of ultrasound within a tissue; and fs is a signal sampling frequency.

4. The pulsed Doppler ultra-high spectral resolution imaging processing system according to claim 3, wherein the computer device is further configured to:

M1, initialize an initial energy value and an initial number of sampling points corresponding to each data point in the velocity sequence for display to 0;

M2, sequentially query the velocity distribution matrix with each data point in the velocity sequence for display, acquire an accumulative coefficient according to a predetermined rule depending on a velocity of each data point in the velocity sequence for display, the size of each matrix velocity point in the velocity distribution matrix and coordinate values of each matrix velocity point, and acquire a matrix energy value corresponding to each accumulative coefficient in the energy distribution matrix; and M3, acquire, according to the matrix energy value obtained for each data point in the velocity sequence for display and the accumulative coefficient, a total energy value corresponding to each data point in the velocity sequence for display to form an energy sequence corresponding to the velocity sequence for displaying a final spectrum.

* * * * *